(12) United States Patent
Nishitani et al.

(10) Patent No.: US 8,591,487 B2
(45) Date of Patent: Nov. 26, 2013

(54) ABSORBENT ARTICLE INCLUDING A SURFACE MEMBER WITH CONCAVED SECTIONS

(75) Inventors: Kazuya Nishitani, Kagawa (JP); Masashi Kitagawa, Tokyo (JP)

(73) Assignee: Uni-Charm Corporation, Ehime (JP)

( * ) Notice: Subject to any disclaimer, the term of this patent is extended or adjusted under 35 U.S.C. 154(b) by 483 days.

(21) Appl. No.: 12/444,682

(22) PCT Filed: Nov. 21, 2007

(86) PCT No.: PCT/JP2007/072548
§ 371 (c)(1),
(2), (4) Date: May 12, 2009

(87) PCT Pub. No.: WO2008/065945
PCT Pub. Date: Jun. 5, 2008

(65) Prior Publication Data
US 2010/0010464 A1    Jan. 14, 2010

(30) Foreign Application Priority Data
Nov. 27, 2006  (JP) ................. 2006-319365

(51) Int. Cl.
*A61F 13/15*    (2006.01)
*A61F 13/20*    (2006.01)

(52) U.S. Cl.
USPC .................... 604/385.01; 604/379

(58) Field of Classification Search
USPC ............ 604/367, 385.01, 379–380, 383–384
See application file for complete search history.

(56) References Cited

U.S. PATENT DOCUMENTS 4,863,785 A  9/1989 Berman et al.
5,608,322 A  3/1997 Lonergan et al.
5,613,960 A  3/1997 Mizutani
6,733,610 B2 * 5/2004 Mizutani et al. .............. 156/164
2002/0068150 A1  6/2002 Taneichi et al.

FOREIGN PATENT DOCUMENTS

| JP | 50111490 | 9/1975 |
| JP | 02-102046 A | 4/1990 |
| JP | 02-133643 A | 5/1990 |
| JP | 8504136 A | 5/1996 |

(Continued)

OTHER PUBLICATIONS

PCT/JP2007/072548 International Search Report.

(Continued)

*Primary Examiner* — Michele M Kidwell
(74) *Attorney, Agent, or Firm* — Lowe Hauptman & Ham, LLP

(57) ABSTRACT

There is provided an absorbent article having a surface member joined in consideration of absorptivity.

The absorbent article has a longitudinal direction, a width direction, and a thickness direction and is worn on a body. The absorbent article includes: an absorbent member for absorbing fluid; and a fluid-permeable surface member, wherein the surface member covers the absorbent member on the side of the body when worn in the thickness direction, the surface member includes a surface sheet and an intermediate sheet that is disposed closer to the absorbent member than the surface sheet in the thickness direction, the surface sheet has a first concave section along a first direction, the intermediate sheet has a second concave section along a second direction that intersects the first direction, and the surface sheet and the intermediate sheet are joined at positions where the first concave section and the second concave section intersect each other.

16 Claims, 9 Drawing Sheets

(56) References Cited

FOREIGN PATENT DOCUMENTS

| JP | 10000712 | 1/1998 |
| JP | 2004181086 | 7/2004 |
| JP | 2004-298454 A | 10/2004 |

OTHER PUBLICATIONS

Supplementary European Search Report dated Jun. 13, 2013 corresponds to European Patent Application No. 07832278.1.

* cited by examiner

A-A CROSS-SECTION

B-B CROSS-SECTION

SURFACE

BACK FACE

ABSORBENT ARTICLE INCLUDING A SURFACE MEMBER WITH CONCAVED SECTIONS

RELATED APPLICATIONS

The present application is based on, International Application PCT/JP2007/072548 filed, Nov. 21, 2007 which claims priority from, Japan Application Number 2006-319365, filed Nov. 27, 2006, the disclosures of which are hereby incorporated by reference herein in their entirety.

TECHNICAL FIELD

The present invention relates to an absorbent article for absorbing fluid.

BACKGROUND ART

It is conventionally known that in order to absorb certain fluid, for example, menstrual blood, an absorbent article has an absorbent member for absorbing a fluid, and a surface member provided between the absorbent member and a human body in order that fluid discharged from the human body may be absorbed by the absorbent member as soon as possible and be moved away from the human body. It is also known that as a surface member of such an absorbent article, a product is used that is obtained, for example, by sending a thermoplastic film and a fibrous layer in an overlapped manner into a gap between two heated rollers, and melting the thermoplastic film with an embossing pattern provided on one of the rollers and a circumferential face, without any projections and depressions on the surface, of the other roller, thereby joining the thermoplastic film and the fibrous layer with opening sections or small embossed sections formed (for example, see JP-A-02-102046).

DISCLOSURE OF INVENTION

Problem to be Solved by the Invention

The above-described surface member of the absorbent article is constituted by the two members such as the thermoplastic film and the fibrous layer, and the two members are joined in an overlapped manner with opening sections or small embossed sections formed. However, an action of the joined sections constituted by the opening sections or small embossed sections on the absorptivity of fluid has not been considered.

The invention was made in view of the conventional problem, and it is an advantage thereof to provide an absorbent article having a surface member joined in consideration of absorptivity.

Means for Solving the Problem

In order to solve the above-described problem, a primary aspect of the invention is an absorbent article that has a longitudinal direction, a width direction, and a thickness direction, and that is worn on a body, including: an absorbent member for absorbing fluid; and a fluid-permeable surface member, wherein the surface member covers the absorbent member on the side of the body when worn in the thickness direction, the surface member includes a surface sheet and an intermediate sheet that is disposed closer to the absorbent member than the surface sheet in the thickness direction, the surface sheet has a first concave section along a first direction, the intermediate sheet has a second concave section along a second direction that intersects the first direction, and the surface sheet and the intermediate sheet are joined at positions where the first concave section and the second concave section intersect each other.

LIST OF REFERENCE NUMERALS

Figure 1:
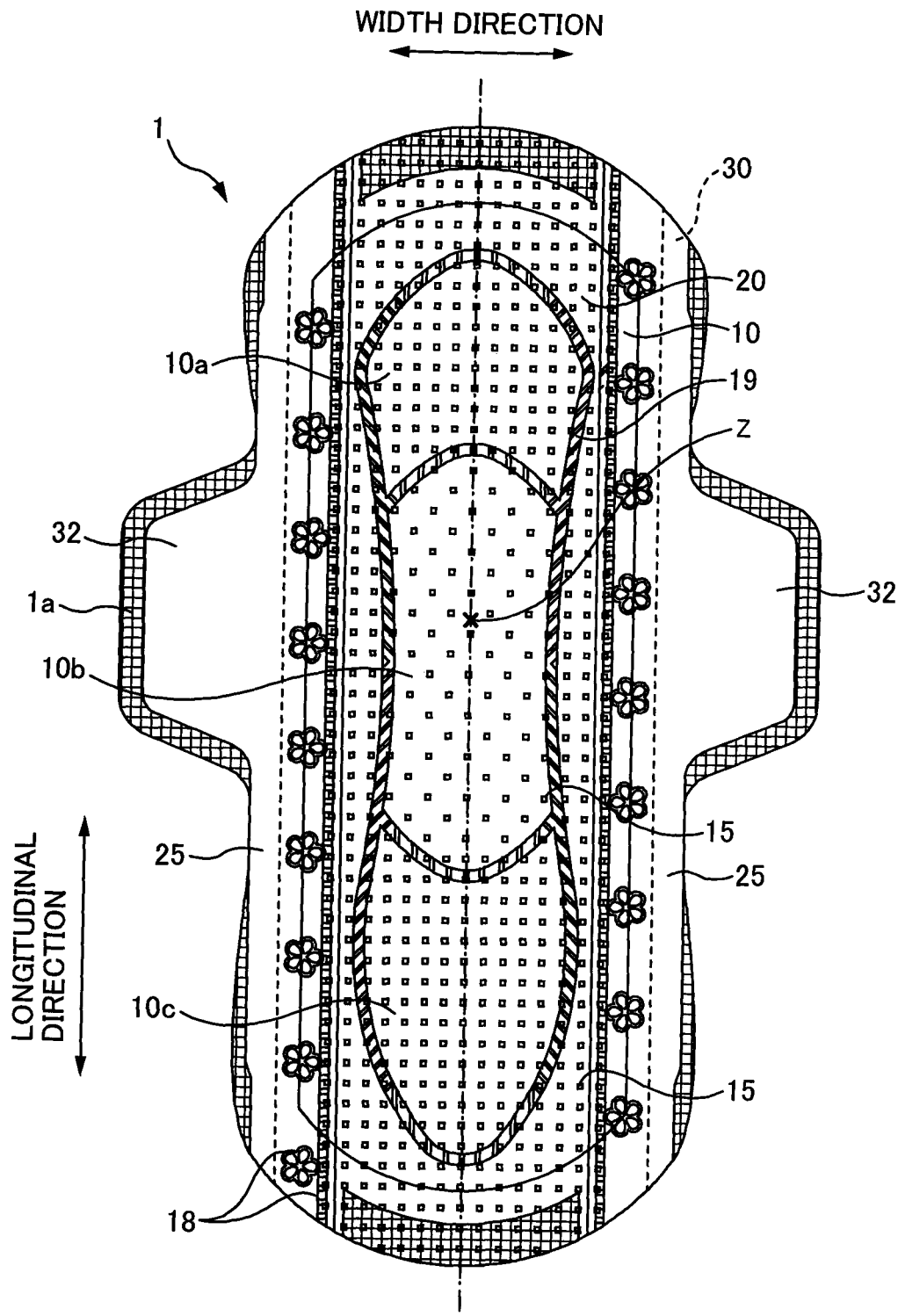
FIG. 1 This is a plan view showing the surface side of an absorbent article according to an embodiment of the invention.

| | |
|---|---|
| 1 | absorbent article, |
| 1a | round seal section, |
| 2 | absorbent article, |
| 10 | absorbent member, |
| 10a | first region, |
| 10b | second region, |
| 10c | third region, |
| 12 | absorbent body material, |
| 14 | surface sheet, |
| 14a | lengthwise concave section, |
| 15 | joined section, |
| 16 | intermediate sheet, |
| 16a | crosswise concave section, |
| 16b | narrow crosswise concave section, |
| 18 | shallow-groove section, |
| 19 | deep-groove section, |
| 20 | surface member, |
| 25 | side sheet, |
| 30 | back face sheet, |
| 32 | holding section, |
| 50 | upper roller, |
| 50a | linear protrusion, |
| 50b | segmented protrusion, |
| 51 | lower roller, |
| 51a | annular protrusion, |
| 52 | guide roller, |
| 52a | annular protrusion, |
| 53 | upper roller, |
| 53a | linear protrusion, |
| Z | assumed position contacting against the bodily discharge opening |

BEST MODE FOR CARRYING OUT THE INVENTION

At least the following matters will be disclosed in the present specification and the drawings.

An absorbent article that has a longitudinal direction, a width direction, and a thickness direction, and that is worn on a body, including: an absorbent member for absorbing fluid; and a fluid-permeable surface member, wherein the surface member covers the absorbent member on the side of the body when worn in the thickness direction, the surface member includes a surface sheet and an intermediate sheet that is disposed closer to the absorbent member than the surface sheet in the thickness direction, the surface sheet has a first concave section along a first direction, the intermediate sheet has a second concave section along a second direction that intersects the first direction, and the surface sheet and the intermediate sheet are joined at positions where the first concave section and the second concave section intersect each other.

With this absorbent article, the surface sheet and the intermediate sheet are joined as described above at positions where the first concave section and the second concave section intersect each other, and thus the absorptivity of the absorbent article can be improved. Herein, the first concave section is formed on the surface of the surface sheet, and recessed toward the intermediate sheet, and the second concave section is formed on the surface of the intermediate sheet, and recessed toward the surface sheet.

In this absorbent article, it is preferable that a plurality of the second concave sections are provided along the second direction, and intersect a plurality of the first concave sections.

With this absorbent article, the plurality of second concave sections are provided along the second direction, and thus a plurality of joined sections can be provided. Thus, the absorptivity of the absorbent article can be improved. Furthermore, the second concave sections are joined to the first concave sections at a plurality of positions, and thus the absorptivity can be further improved.

In this absorbent article, it is preferable that a plurality of the first concave sections are provided along the first direction, and intersect a plurality of the second concave sections.

With this absorbent article, the plurality of first concave sections are provided along the first direction, and thus a plurality of joined sections can be provided. Thus, the absorptivity of the absorbent article can be improved. Furthermore, the first concave sections are joined to the second concave sections at a plurality of positions, and thus the absorptivity of the absorbent article can be further improved.

In this absorbent article, it is preferable that the first direction is a longitudinal direction of the absorbent member.

With this absorbent article, the first concave sections are provided in the longitudinal direction of the absorbent member, and thus the absorptivity of the absorbent article can be improved.

In this absorbent article, it is preferable that the surface sheet and the intermediate sheet are nonwoven fabric containing thermally melting fiber, and that the joined sections are thermally fused.

With this absorbent article, the surface sheet and the intermediate sheet can be joined by thermal fusion, and thus an absorbent article having high absorptivity can be provided without performing complicated operations such as application of an adhesive and the like. Furthermore, for example, if the absorbent article is an absorbent article that absorbs fluid such as menstrual blood, an absorbent article can be provided in which the fused section hardly slips off even when the wearer wearing the absorbent article vigorously moves. When worn, the first concave sections are recessed from the surface contacting against the skin toward clothing, and the second concave sections are recessed from the face contacting against the absorbent member toward the body.

Embodiments

Hereinafter, the outline of the configuration of an absorbent article according to an embodiment of the invention shall be described. The absorbent article of this embodiment is a sanitary napkin. In the following description, the side that is brought into contact with the body is referred to as a surface side, the side that is brought into contact with an undergarment is referred to as a back face side, an end that is positioned on the front side of the human body when worn is referred to as a front end, and an end that is positioned on the rear side is referred to as a rear end.

Figure 2:
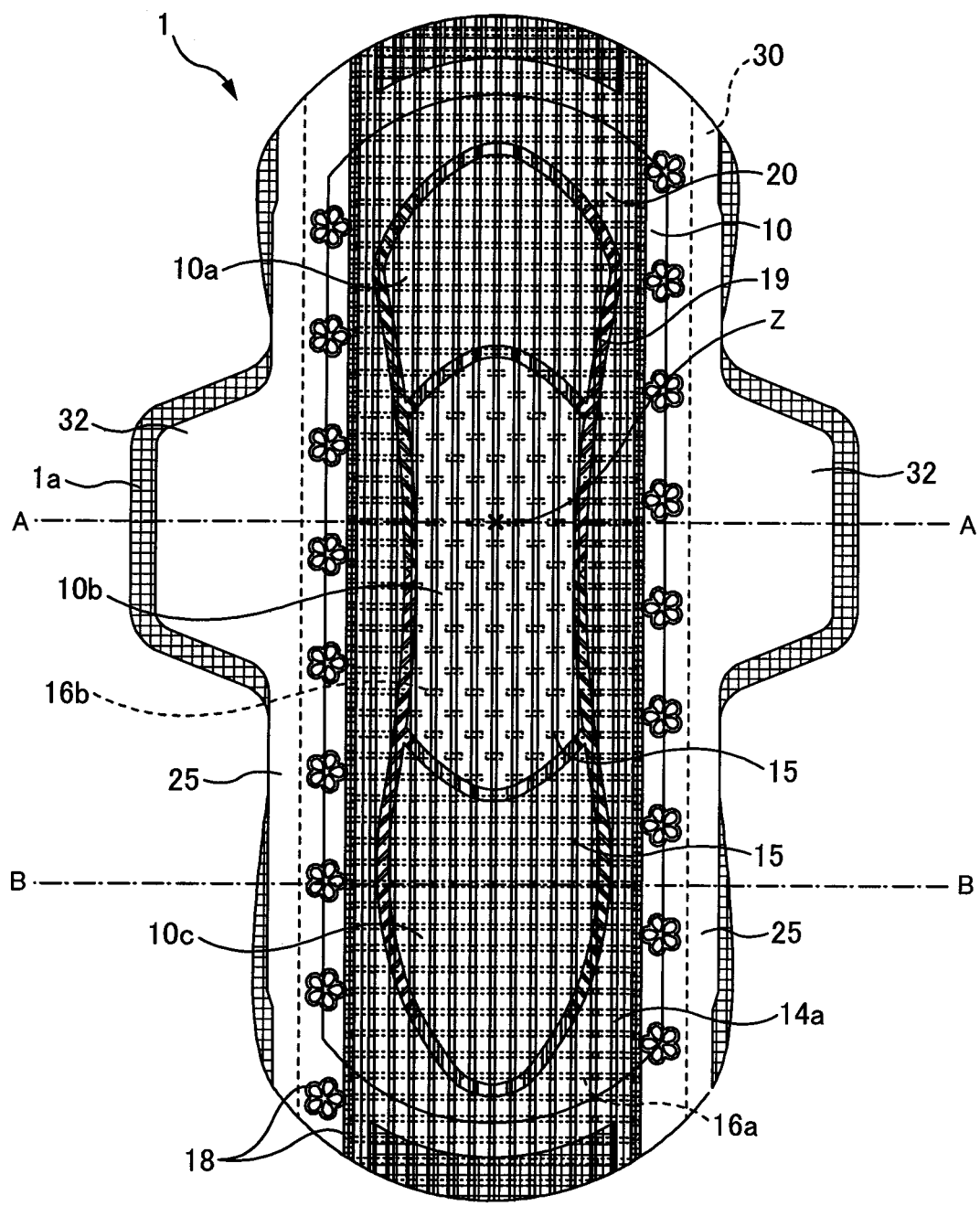
FIG. 2 This a plan view for illustrating lengthwise concave sections and crosswise concave sections formed on the absorbent article according to this embodiment.
Figure 3:
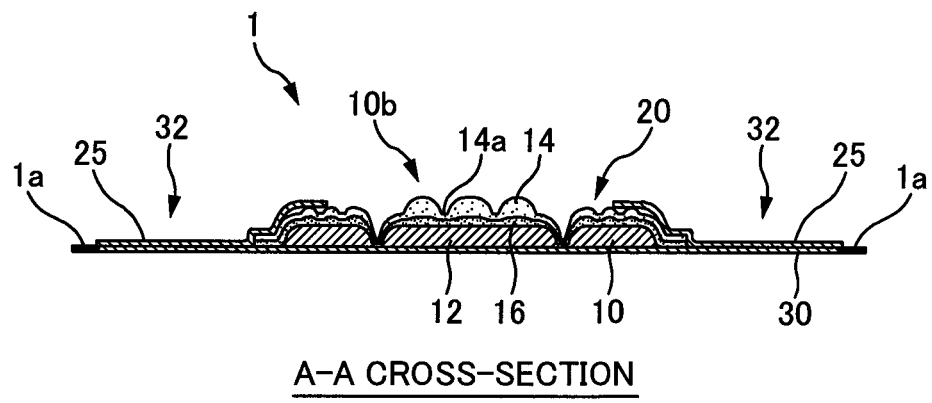
FIG. 3 This is a cross-sectional view taken along the line A-A in FIG. 2.
Figure 4:
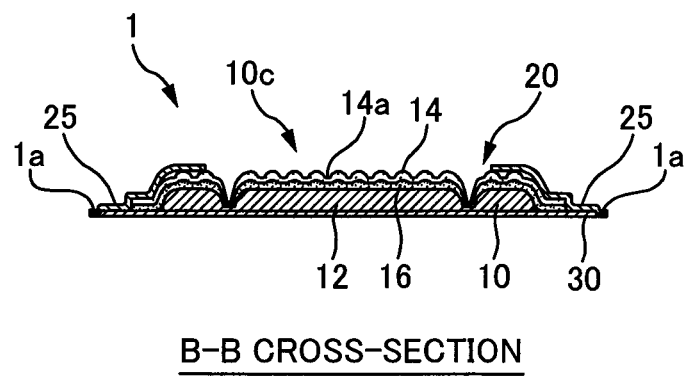
FIG. 4 This is a cross-sectional view taken along the line B-B in FIG. 2.

FIG. 1 is a plan view showing the surface side of the absorbent article according to this embodiment. FIG. 2 is a plan view for illustrating lengthwise concave sections and crosswise concave sections formed on the absorbent article according to this embodiment. FIG. 3 is a cross-sectional view taken along the line A-A in FIG. 2. FIG. 4 is a cross-sectional view taken along the line B-B in FIG. 2.

As shown FIGS. 1 to 4, an absorbent article 1 in this embodiment is elongated in a predetermined direction, and has a substantially rectangular absorbent member 10 for absorbing fluid such as menstrual blood, a back face sheet 30 provided on the back face of the absorbent member 10, a fluid-permeable surface member 20 covering the surface side of the absorbent member 10, and side sheets 25 arranged on both sides of the absorbent member 10 in a direction intersecting the longitudinal direction.

In the absorbent article 1 of this embodiment, an assumed position Z contacting against the bodily discharge opening at which the bodily discharge opening is assumed to come into contact against the absorbent article 1 is positioned closer to the front end than the middle in the longitudinal direction, on the center line in the width direction of the absorbent article 1.

The absorbent member 10 has an absorbent body material 12 and thin paper (not shown) such as tissue paper and the like, the absorbent body material 12 being made of pulverized pulp, obtained by pulverizing sheet-like pulp, and a super absorbent polymer. The absorbent body material 12 in the form of a sheet having a predetermined thickness is wrapped in the thin paper. Herein, the thin paper is a sheet that is fluid-permeable and has smaller openings than particles of the superabsorbent polymer so as to prevent the superabsorbent polymer from leaking out of the thin paper. It should be noted that the absorbent body material 12 may contain thermally melting fiber in order to prevent deformation in use.

The back face sheet 30 is a thermoplastic and fluid-impermeable sheet made of materials such as polyethylene or polypropylene. The back face sheet 30 is sufficiently wider than the absorbent member 10. Throughout the entire periphery, the outer edge portion of the back face sheet 30 is positioned outside the outer edge portion of the absorbent member 10. Furthermore, on both sides in a direction intersecting the longitudinal direction (hereinafter, referred to as a width direction), holding sections 32 extending outward in the width direction are formed in a predetermined region centered, in the longitudinal direction, at the assumed position Z contacting against the bodily discharge opening.

The surface member 20 is slightly wider than the absorbent member 10 in the width direction, is substantially as long as the back face sheet 30 in the longitudinal direction, and covers the entire area of the surface of the absorbent member 10. The surface member 20 is described later in detail.

The side sheets 25 are appropriate nonwoven fabric made of synthetic resin fibers, such as air-through nonwoven fabric, spunbonded nonwoven fabric, or nonwoven fabric including spunbonded-meltblown-spunbonded layers.

In the absorbent article 1, the surface member 20 is joined with a hot-melt adhesive to the surface side of the absorbent member 10, and a deep-groove section 19 is formed at a predetermined position by deep-groove embossing in which pressing is performed in the thickness direction using a pressing member heated to high temperature. The deep-groove section 19 formed by deep-groove embossing joins the absorbent member 10 and the surface member 20 more tightly. Furthermore, the formed deep-groove section 19 serves as a curve-inducing section for forming a curve such that the absorbent article 1 easily fits along the body when worn. In this embodiment, three regions are defined by the deep-groove section 19. In the following description, the three regions are referred to as a first region 10a, a second region 10b, and a third region 10c, from the side of the front end along the longitudinal direction.

The back face sheet 30 is joined with a hot-melt adhesive to the absorbent member 10 and the surface member 20 on the back face side. Furthermore, on the surface side, the side sheets 25 are joined with a hot-melt adhesive to an area from positions slightly overlapped with both side portions of the absorbent member 10 to the back face sheet. Line-like and flower-like shallow-groove sections 18 are formed by embossing using a pressing member heated to low temperature at positions where the surface member 20 and the side sheets 25 are overlapped. The shallow-groove sections 18 join the surface member 20 and the side sheets 25 more tightly.

The outer edge portion of the absorbent article 1 is subjected to round sealing in which thermal fusion is performed at low temperature, and forms a reinforced round seal section 1a.

The surface member 20 has a double-layered structure constituted by a surface sheet 14 that is disposed on the outside in the absorbent article 1, and an intermediate sheet 16 that is between the surface sheet 14 and the absorbent member 10.

As materials of the surface sheet 14 and the intermediate sheet 16, nonwoven fabric containing appropriate thermally melting fibers are used, and examples thereof include air-through nonwoven fabric made of cellulose fibers such as rayon or synthetic resin fibers, and spunlaced nonwoven fabric made of synthetic resin fibers or the like. The surface sheet 14 is positioned on the surface side that is brought into contact with the body, and thus the surface sheet 14 is a sheet softer than the thin paper. Furthermore, the intermediate sheet 16 is a highly fluid-permeable member that is denser than the surface sheet 14. When the intermediate sheet 16 is provided between the surface sheet 14 and the absorbent member 10, fluid that has permeated the surface sheet 14 is moved toward the intermediate sheet 16 drawing in more fluid than the surface sheet 14.

Figure 5:
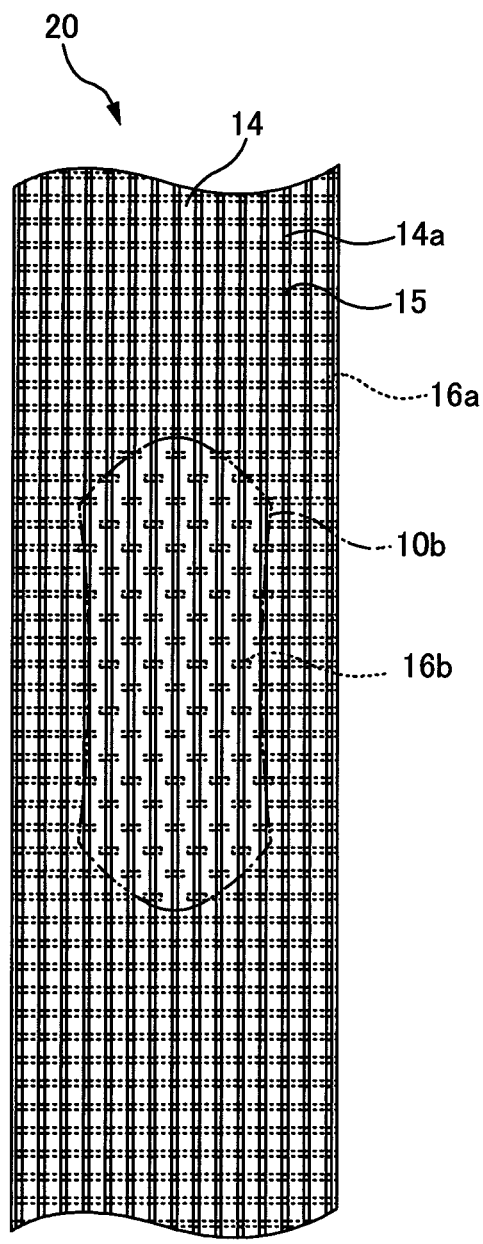
FIG. 5 This is a view showing a surface of a surface member according to this embodiment.
Figure 6:
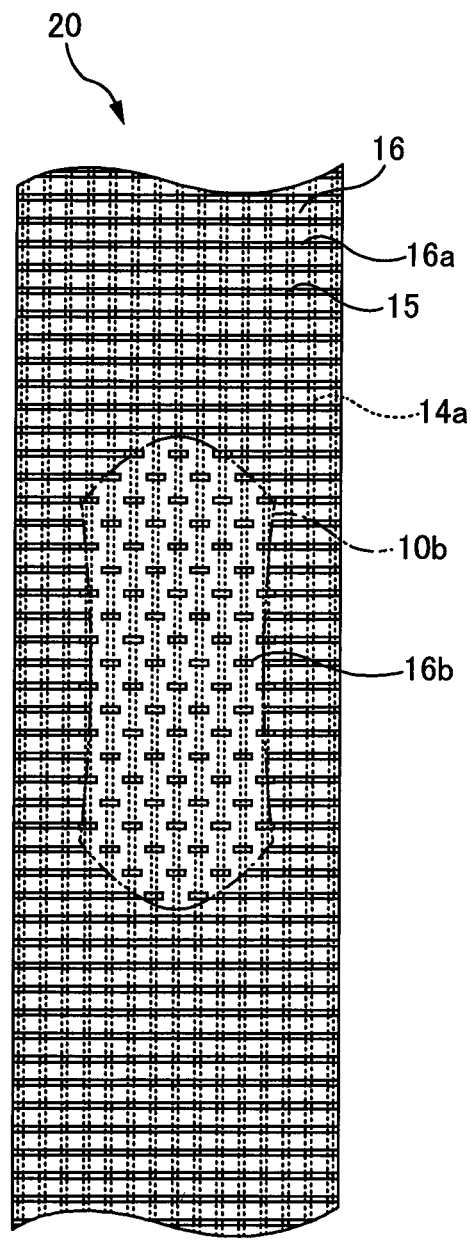
FIG. 6 This is a view showing a back face of the surface member according to this embodiment.

FIG. 5 is a view showing the surface of the surface member according to this embodiment. FIG. 6 is a view showing the back face of the surface member according to this embodiment. In FIGS. 5 and 6, for the sake of convenience of this description, a position corresponding to the second region when joined to the absorbent member 10 is indicated by a dashed-dotted line.

The surface member 20 is provided so as to cover the absorbent member 10. In a central predetermined region on the absorbent member 10, which is in the vicinity of the assumed position Z contacting against the bodily discharge opening on the absorbent article 1, the density of joined sections 15 subjected to thermal fusion is lower than that of the other regions. In this embodiment, among the three regions 10a, 10b, and 10c defined by deep-groove embossing, a region including the assumed position Z contacting against the bodily discharge opening, that is, the second region 10b positioned in the middle of the three defined regions 10a, 10b, and 10c corresponds to the central predetermined region, and the density of the joined sections 15 is low in this region.

Lengthwise concave sections 14a, as a plurality of first concave sections continuously formed along the longitudinal direction as a first direction, are provided spaced away from each other as appropriate in the width direction, throughout the entire area of the surface sheet 14 constituting the surface member 20. That is to say, the plurality of lengthwise concave sections 14a are provided from the front end of the absorbent article 1 toward the rear end, and the profile on the surface side obtained by cutting the surface sheet 14 in the width direction are in the form of waves.

Crosswise concave sections 16a, as a plurality of second concave sections continuously formed along the width direction as a second direction, are provided spaced away from each other as appropriate in the longitudinal direction, on the intermediate sheet 16 excluding the second region 10b. Furthermore, a plurality of narrow crosswise concave sections 16b, as a plurality of third concave sections, continued to the crosswise concave sections 16a that are provided on both sides of the second region 10b in the width direction are provided spaced away from each other as appropriate in the second region 10b. More specifically, in the second region 10b, the plurality of narrow crosswise concave sections 16b are provided along the width direction of the absorbent article 1. The narrow crosswise concave sections 16b are arranged so as to intersect every other lengthwise concave section 14a of the plurality of lengthwise concave sections 14a provided spaced away from each other as appropriate in the width direction.

The surface sheet 14 and the intermediate sheet 16 are overlapped such that the lengthwise concave sections 14a and the crosswise concave sections 16a and 16b intersect each other at substantially right angles, and the lengthwise concave sections 14a of the surface sheet 14 and the crosswise concave sections 16a and 16b of the intermediate sheet 16 are joined by thermal fusion at positions where the concave sections intersect each other, and thus the surface member 20 is integrally formed. The dot-like joined sections 15 are formed by thermal fusion at portions where the lengthwise concave sections 14a and the crosswise concave sections 16a and 16b intersect each other. More specifically, since the lengthwise concave sections 14a, which are thin wall portions of the surface sheet 14, and the crosswise concave sections 16a and 16b, which are thin wall portions of the intermediate sheet 16, are thermally fused to each other, thick wall portions of the surface sheet 14 and the intermediate sheet 16 outside the lengthwise concave sections 14a and the crosswise concave sections 16a and 16b are not compressed by joining the surface sheet 14 and the intermediate sheet 16, and thus no joined section 15 is formed therein. Thus, a portion of the surface member 20 in which the lengthwise concave sections 14a and the crosswise concave sections 16a and 16b are not formed is as thick as the surface sheet 14 and the intermediate sheet 16 that are not pressed.

In the surface member 20 of this embodiment, in a region outside the second region 10b, portions of the lengthwise concave sections 14a provided on the surface sheet 14 projecting toward the intermediate sheet 16 and portions of the crosswise concave sections 16a provided on the intermediate sheet 16 projecting toward the surface sheet 14 are on a grid, and all the concave sections are joined at positions where they intersect each other (hereinafter, referred to as intersecting points) to form the joined sections 15. On the other hand, in the second region 10b, joined sections 15 are formed at positions where portions of the lengthwise concave sections 14a provided on the surface sheet 14 projecting toward the intermediate sheet 16 and portions of the narrow crosswise concave sections 16b provided on the intermediate sheet 16 projecting toward the surface sheet 14 intersect each other. Thus, the joined sections 15 formed in the second region are alternately formed in both the longitudinal direction and the width direction, with respect to the joined sections 15 formed in the region outside the second region. More specifically, a spacing between the adjacent joined sections 15 in the second region 10b is substantially twice as large as a spacing between the adjacent joined sections 15 in the region outside the second region 10b, in both the longitudinal direction and the width direction. Thus, the second region 10b is thicker than the region other than the second region 10b. Since the second region 10b that is thicker than the other regions and provides tight fitting includes the assumed position Z contacting against the bodily discharge opening, the second region 10b fits to the bodily discharge opening when worn, and thus discharged fluid can be reliably absorbed and prevented from leaking to the outside. Furthermore, since the second region 10b is thick, and thus excellent cushioning properties and good feel are provided.

Moreover, since the surface sheet 14 of this embodiment is provided with the lengthwise concave sections 14a continuously formed along the longitudinal direction, gaps are formed in the front-and-rear direction when worn between the surface sheet 14 and the body, and thus the air permeability is improved. Thus, the air permeability is secured at the region other than the second region 10b, which is comparatively away from the assumed position Z contacting against the bodily discharge opening, and thus discomfort of the wearer is alleviated by suppressing stuffiness and the like. Accordingly, it is possible to provide the absorbent article 1 that can be comfortably used.

Figure 7:
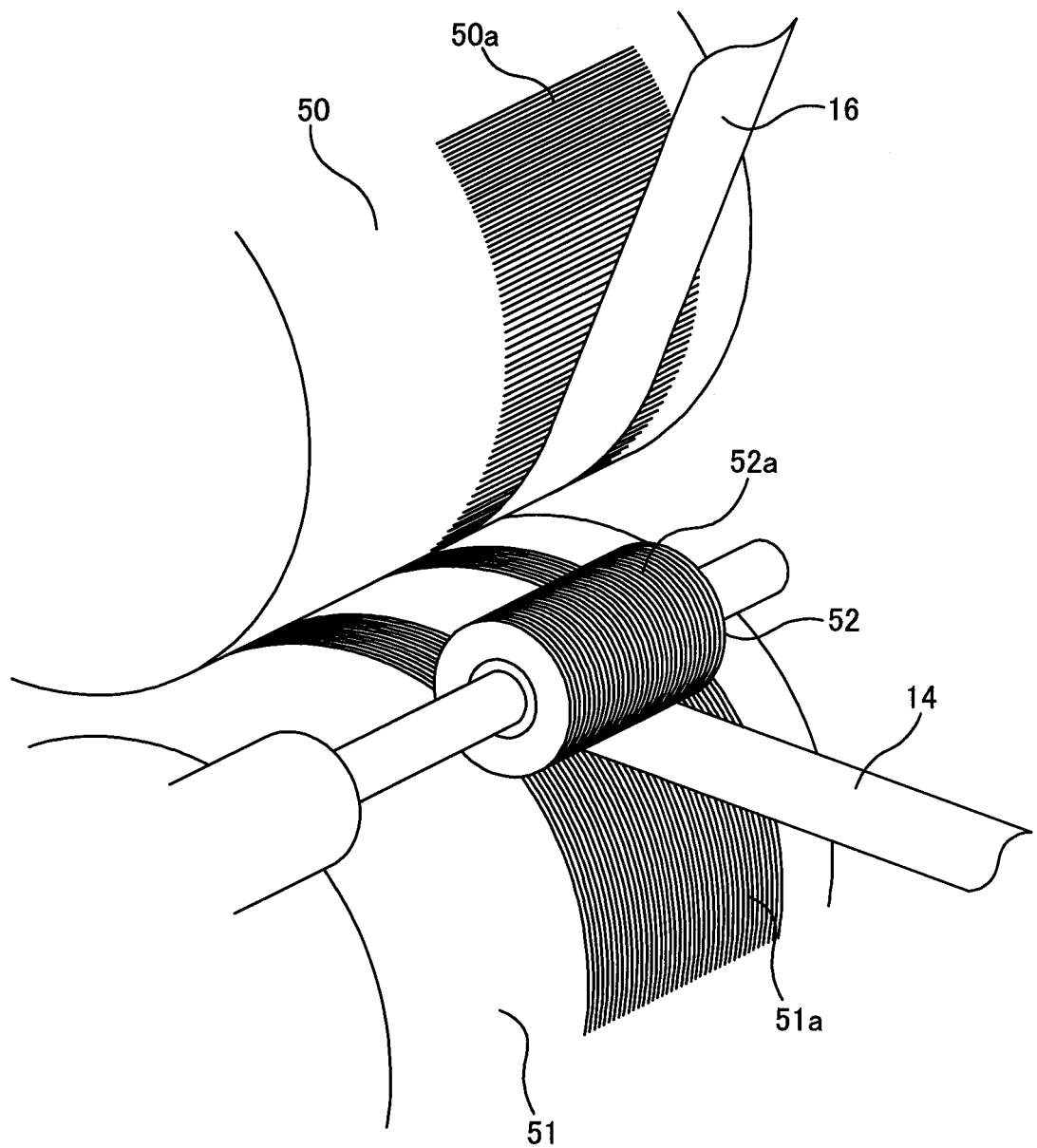
FIG. 7 This is a view for illustrating a method for producing the surface member.
Figure 8:
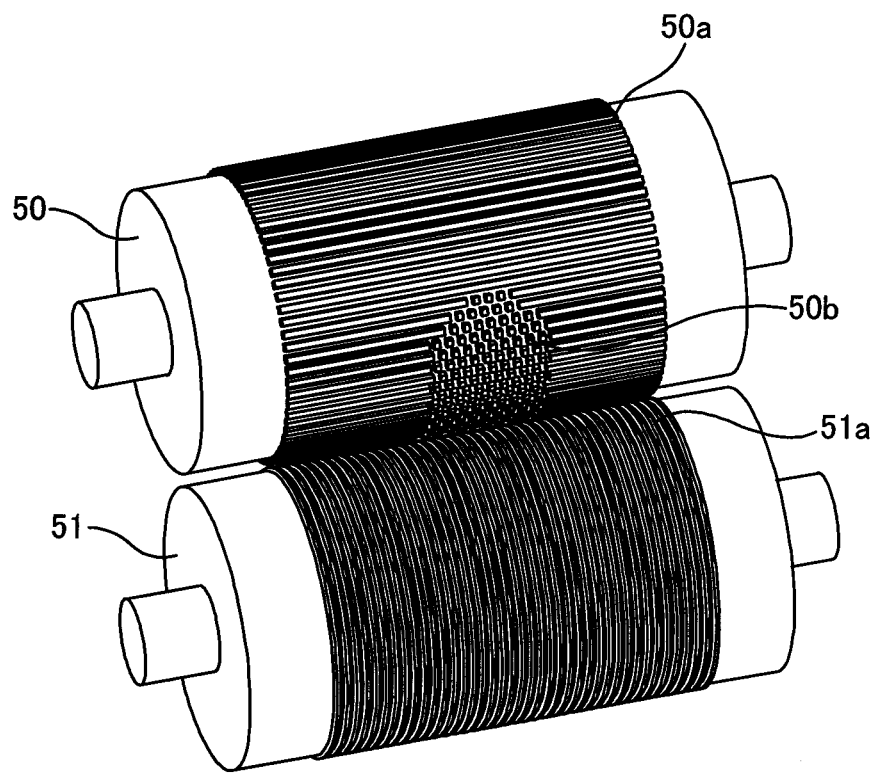
FIG. 8 This is a conceptual diagram for illustrating the surface shape of a pair of rollers for producing the surface member.

The surface member 20 of this embodiment is produced by, for example, the following method. FIG. 7 is a view for illustrating a method for producing the surface member. FIG. 8 is a conceptual diagram for illustrating the surface shape of a pair of rollers for producing the surface member.

As shown in FIG. 7, regarding the surface member 20, the surface sheet 14 and the intermediate sheet 16 are supplied from below and above respectively to a gap between two rollers 50 and 51 that are held by shafts provided in the same direction and opposed to each other in the vertical direction.

As shown in FIG. 8, a plurality of rib-like annular protrusions 51a extending in the circumferential direction are provided spaced away from each other in the axial direction, on the lower roller 51 disposed on the side of the surface sheet 14. A plurality of rib-like linear protrusions 50a extending along the axial direction are provided spaced away from each other in the circumferential direction, on the upper roller 50 disposed on the side of the intermediate sheet 16. When the upper and lower rollers 50 and 51 rotate, the surface sheet 14 and the intermediate sheet 16 supplied to a gap between the rollers are pressed and joined at positions where the annular protrusions 51a and the linear protrusions 50a are opposed to each other.

In order to form the narrow crosswise concave sections 16b, segmented protrusions 50b obtained by segmenting the linear protrusions 50a in the axial direction are provided in a portion of the upper roller 50 for joining a portion at the position corresponding to the second region 10b of the surface member 20. The segmented protrusions 50b are arranged so as to be opposed to every other annular protrusion 51a, in the width direction, of the plurality of annular protrusions 51a provided on the lower roller 51. Also in the circumferential direction, the segmented protrusions 50b are arranged so as to be opposed to every other annular protrusion 51a, in the circumferential direction, of the plurality of annular protrusions 51a provided on the lower roller 51.

Before the surface sheet 14 is overlapped with the intermediate sheet 16 and held between the upper and lower rollers 50 and 51, the surface sheet 14 is placed along the lower roller 51 and curved by a guide roller 52 provided in opposition to the lower roller 51, and thus the lengthwise concave sections 14a are formed. The guide roller 52 has annular protrusions 52a formed at a pitch equal to the annular protrusions 51a of the lower roller 51. The tip ends of the annular protrusions 51a and 52a are loosely engaged with each other without being in contact with the rollers 51 and 52 opposed thereto. Thus, the lengthwise concave sections 14a are formed on the surface sheet 14 from a position at which the surface sheet 14 passes through a gap between the lower roller 51 and the guide roller 52. At that time, the lower roller 51 has been heated to a temperature close to the melting point of thermally melting fibers contained in the surface sheet 14. Thus, even without a great pressing force, the lengthwise concave sections 14a are formed to the extent that their cross-section is undulated.

On the other hand, before the intermediate sheet 16 is overlapped with the surface sheet 14 and held between the upper and lower rollers 50 and 51, the intermediate sheet 16 is placed along the upper roller 50 with a tensile force applied thereto, and thus the crosswise concave sections 16a and 16b are formed. At that time, the upper roller 50 has been heated to a temperature close to the melting point of thermally melting fibers contained in the intermediate sheet 16. Thus, even without a great pressing force, the crosswise concave sections 16a and 16b are formed to the extent that their cross-section is undulated. At that time, of the lengthwise concave sections 14a and the crosswise concave sections 16a and 16b formed before being held between the upper and lower rollers 50 and 51, the lengthwise concave sections 14a curved by the guide roller 52 is more clearly shaped than the crosswise concave sections 16a and 16b.

The surface sheet 14 on which the lengthwise concave sections 14a are formed and the intermediate sheet 16 on which the crosswise concave sections 16a and 16b are formed are pressed and thermally fused at positions where the annular protrusions 51a and the linear protrusions 50a are opposed to each other, in a state where the surface sheet 14 and the intermediate sheet 16 are overlapped between the heated upper and lower rollers 50 and 51, as described above.

The inventors of this absorbent article confirmed the absorptivity of the absorbent article 1 by the following test, the absorbent article 1 using the surface member 20 in which the surface sheet 14 has the lengthwise concave sections 14a, the intermediate sheet 16 has the crosswise concave sections 16a and 16b, and the lengthwise concave sections 14a and the crosswise concave sections 16a and 16b are joined at positions where the concave sections intersect each other, as described in the foregoing embodiment.

Comparative Test on Absorptivity
Outline of the Test

Artificial menstrual blood is repeatedly dropped onto a surface of a test piece corresponding to absorbent articles, and the heat transfer rate (Qmax) is measured each time after dropping. At that time, as an apparatus for measuring heat transfer rate (Qmax), a Finger-robot thermo labo (produced by KES Kato tech Co., Ltd.) is used.

Heat transfer rate (Qmax) is originally for measuring "coldness/warmth when an article is touched", and the value tends to be higher as the amount of fluid remaining on the surface of a surface sheet is larger. Thus, the degree of fluid remaining on the surface of a surface sheet (absorptivity of an absorbent article) is indicated by heat transfer rate (Qmax). If the absorptivity of an absorbent article (test piece) is high, the amount of fluid remaining on the surface of the surface sheet is small, and thus the value of heat transfer rate (Qmax) is small. As the artificial menstrual blood, fluid having a viscosity of approximately 22 to 26 mPa·s is prepared in advance.

Test Piece

Surface members are overlapped on absorbent members, and their both side portions are subjected to embossing, and thus test pieces are formed. The following absorbent members and surface members are used. Hereinafter, a test piece on which a first surface member is overlapped is referred to as a first test piece, a test piece on which a second surface member is overlapped is referred to as a second test piece, and a test piece on which a third surface member is overlapped is referred to as a third test piece.

Absorbent Member

Non-treated pulp or treated pulp is wrapped in tissue paper, and cut into a size of 100 mm (length)×60 mm (width) for use. The weight per unit area of the pulp is adjusted to 500 g/m², and the density is to 0.09 g/cm³.

Surface Member

The surface sheet and the intermediate sheet are overlapped, embossed, joined, and then cut into a size of 100 mm (length)×60 mm (width). Herein, for the sake of comparison, three types of surface members below are used. All the surface members are air-through nonwoven fabric using polypropylene/polyester compound fiber.

First Surface Member

Surface member (corresponding to a conventional product) obtained by embossing with a roller whose circumferential face has a plurality of protrusions and a roller whose surface is smooth. The weight per unit area is 30 g/m².

Second Surface Member

Surface member (same as the region other than the second region in the foregoing embodiment) in which a surface sheet is provided with lengthwise concave sections, an intermediate sheet is provided with crosswise concave sections, and the lengthwise concave sections and the crosswise concave sections are joined at all the intersecting points thereof. The weight per unit area is 40 g/m².

Third Surface Member

Surface member (same as the second region in the foregoing embodiment) in which the embossing density is lower than that of the second surface member. The weight per unit area is 40 g/m².

Test Procedure

1. An acrylic plate in which an opening is formed at the center is placed on the surface member of the test piece. Herein, the acrylic plate has a size of, for example, 200 mm (length)×100 mm (width), an opening size of 40 mm×10 mm, and a weight of approximately 125 g.

2. A nozzle of an autoburette for dropping the artificial menstrual blood is disposed 10 mm from the upper face of the acrylic plate, above the opening of the acrylic plate.

3. The artificial menstrual blood is dropped on the test piece (first dropping: dropping amount 3 ml, dropping rate 95 mil/min).

4. At 60 seconds after starting the dropping of the artificial menstrual blood, the heat transfer rate at the surface of the surface member is measured (first measurement). More specifically, a contact temperature sensor of the Finger-robot thermo labo is brought into contact against the test piece at a position onto which the artificial menstrual blood was dropped. Herein, a jig is used in order to prevent a change in measurement conditions such as pressure of the contact temperature sensor that is brought into contact with the test piece every time in the repeated measurements.

5. After the first measurement of the heat transfer rate, the artificial menstrual blood is dropped onto the test piece (second dropping: dropping amount 4 ml, dropping rate 95 ml/min).

6. At 60 seconds after starting the second dropping of the artificial menstrual blood, the heat transfer rate at the surface of the surface member is measured (second measurement).

7. After the second measurement of the heat transfer rate, the artificial menstrual blood is dropped onto the test piece (third dropping: dropping amount 3 ml, dropping rate 95 ml/min).

8. At 60 seconds after starting the third dropping of the artificial menstrual blood, the heat transfer rate at the surface of the surface member is measured (third measurement).

Following the above-described procedure, the heat transfer rate (Qmax) is measured on five test pieces in each measurement, and is evaluated based on the measured values.

(Reference) rough standard between the Qmax value and the contact feel

Qmax Value

| 0 to 0.30 | hardly feel cold (hardly feel wet) |
| 0.30 to 0.50 | slightly cold (slightly feel wet) |
| 0.50 or more | cold (feel wet) |

Measurement Results

|  | 1st test piece | 2nd test piece | 3rd test piece |
|---|---|---|---|
| Qmax × 1st measurement | 0.172 | 0.096 | 0.082 |
| Qmax × 2nd measurement | 0.187 | 0.107 | 0.092 |
| Qmax × 3rd measurement | 0.263 | 0.167 | 0.135 |

As shown in Table 1, each time, the second test piece corresponding to the region other than the second region described in the foregoing embodiment and the third test piece corresponding to the second region have Qmax values that are smaller the Qmax value of the first test piece corresponding to a conventional example, more specifically, substantially half of the Qmax value. That is to say, when as in the absorbent article 1 of the foregoing embodiment, the surface member 20 is constituted by the surface sheet 14 and the intermediate sheet 16, the lengthwise concave sections 14a in the longitudinal direction are formed on the surface sheet 14, the crosswise concave sections 16a and 16b are formed on the intermediate sheet 16, and the lengthwise concave sections 14a and the crosswise concave sections 16a and 16b are joined at positions where the concave sections intersect each other, the highly absorptive absorbent article 1 that is provided with the surface member 20 having fluid-permeability higher than conventional absorbent articles is realized.

In the foregoing embodiment, an example was described in which in the second region 10b, the crosswise concave sections 16a are changed into the plurality of narrow crosswise concave sections 16b spaced away from each other in the width direction, and thus spacing between the adjacent joined sections 15 is wider than that in the region other than the second region 10b. However, the crosswise concave sections 16a may be continuously formed along the width direction, and the lengthwise concave sections 14a may be provided as a plurality of narrow lengthwise concave sections spaced away from each other along the longitudinal direction. Furthermore, an example was described in which each of the narrow crosswise concave sections 16b intersects one lengthwise concave section 14a to form one joined section 15. However, each of the narrow crosswise concave sections 16b or narrow lengthwise concave sections may intersect two or more lengthwise concave sections 14a or crosswise concave sections 16a to form a plurality of joined sections 15.

In the foregoing embodiment, an example was described in which the density of the joined sections 15 provided in the second region 10b is lower than the density of the joined sections 15 provided in the region outside the second region 10b. However, the joined sections 15 may be formed at substantially uniform density throughout the entire area of the surface member 20.

Figure 9:
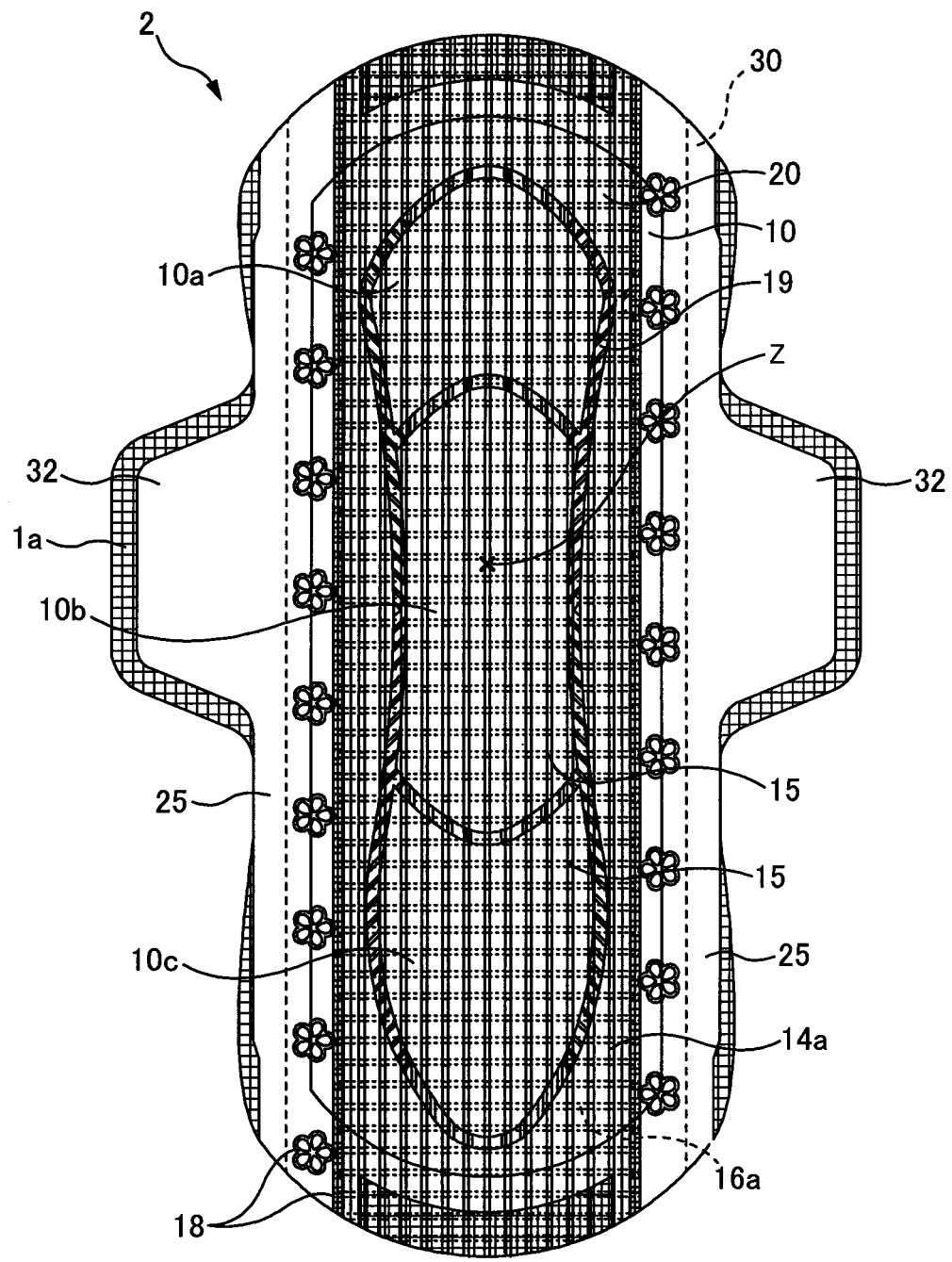
FIG. 9 This is a plan view showing an example of an absorbent article in which joined sections are formed at substantially uniform density throughout the entire area of a surface member.
Figure 10:
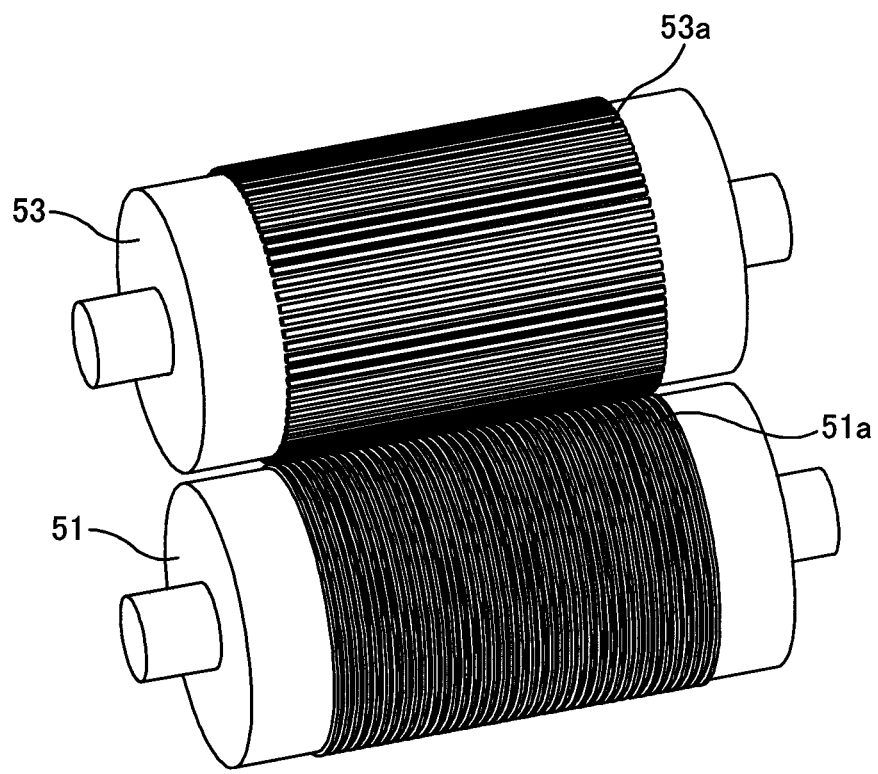
FIG. 10 This is a view for illustrating rollers for forming the surface member in which the joined sections are formed at substantially uniform density throughout the entire area.

FIG. 9 is a plan view showing an example of an absorbent article in which joined sections are formed at substantially uniform density throughout the entire area of a surface member. FIG. 10 is a view for illustrating rollers for forming the surface member in which the joined sections are formed at substantially uniform density throughout the entire area.

For example, as shown in FIG. 9, also in the second region 10b, portions of the lengthwise concave sections 14a provided on the surface sheet 14 projecting toward the intermediate sheet 16 and portions of the crosswise concave sections 16a provided on the intermediate sheet 16 projecting toward the surface sheet 14 may be on a grid as in the region outside the second region 10b, and all the concave sections may be joined at positions where they intersect each other (intersecting points) to form the joined sections 15. For example, as shown in FIG. 10, rollers for producing such a surface member of an absorbent article 2 are constituted by an upper roller 53 that is provided with linear protrusions 53a continuously formed in the width direction throughout the entire circumference, and the lower roller 51 that is provided with the annular protrusions 51a continuously formed in the circumferential direction throughout the entire circumference. The surface sheet 14 and the intermediate sheet 16 are overlapped after being inserted into a gap between the pair of upper and lower rollers 51 and 53, and portions that are held between the annular protrusions 51a and the linear protrusions 53a are joined, and thus the absorbent article 2 can be easily formed in which the joined sections 15 are formed at substantially uniform density throughout the entire area of the surface member 20.

Other Embodiments

For the sake of convenience of this description, in the foregoing embodiment, a configuration was described in which the absorbent member 10 is provided with one absorbent body material 12 in the middle in the width direction. However, there is no limitation to this. For example, side absorbent bodies may be provided along the longitudinal direction respectively on both end portions in the width direction on the absorbent member 10. Alternatively, standing gathers may be provided respectively at the both end portions instead of the side absorbent bodies.

In the foregoing embodiment, an example was described in which the assumed position Z contacting against the bodily discharge opening is positioned closer to the front end than the middle in the longitudinal direction. However, the assumed position Z contacting against the bodily discharge opening may be positioned in the middle in the longitudinal direction.

In the foregoing embodiment, as the back face sheet 30, a thermoplastic and fluid-impermeable sheet made of materials such as polyethylene or polypropylene was used. However, a sheet-like member also may be used in which a thermoplastic and fluid-impermeable sheet is contained, and, for example, thin paper, nonwoven fabric, or other materials are layered.

The foregoing embodiments are merely for the purpose of elucidating the invention and are not to be interpreted as limiting the invention. The invention can of course be altered and improved without departing from the gist thereof and equivalents are intended to be embraced therein.

The invention claimed is:

1. An absorbent article adapted to be worn on a wearer's body and having a longitudinal direction, a width direction, and a thickness direction, said absorbent article comprising:
    an absorbent member for absorbing fluid; and
    a fluid-permeable surface member covering an entire surface of the absorbent member as seen in a plan view in the thickness direction, and adapted to face the body when the absorbent article is worn;
    wherein
    the surface member includes a surface sheet and an intermediate sheet that is disposed closer to the absorbent member than the surface sheet in the thickness direction,
    the surface sheet has at least one first concave section elongated along a first direction, the first concave section being depressed toward the intermediate sheet in the thickness direction,
    the intermediate sheet has at least one second concave section elongated along a second direction that intersects the first direction, the second concave section being depressed toward the surface sheet in the thickness direction,
    the surface sheet and the intermediate sheet are joined at first positions where the first concave section and the second concave section intersect each other,
    said absorbent article has a front end and a rear end opposite the front end in the longitudinal direction, and
    said at least one first concave section extends in the longitudinal direction all the way from the front end to the rear end.

2. The absorbent article according to claim 1, wherein a plurality of the second concave sections intersect a plurality of the first concave sections to define a checker or plaid pattern as seen in the plan view.

3. The absorbent article according to claim 2, wherein the first direction is the longitudinal direction and the second direction is the width direction.

4. The absorbent article according to claim 3, wherein said first concave sections are spaced from each other in the width direction and continuously extend in the longitudinal direction on an entire surface of the surface sheet.

5. The absorbent article according to claim 3, wherein
the surface member has a first region and a second region outside the first region;
the first and second concave sections are formed in the second region;
the intermediate sheet in the first region comprises at least one third concave section that is different from the second concave section and is spaced from the second concave section in the longitudinal direction, and
the surface sheet and the intermediate sheet are joined at second positions where the first concave sections and the third concave sections intersect each other.

6. The absorbent article according to claim 5, wherein the second positions are alternately formed in both the longitudinal direction and the width direction in the second region.

7. The absorbent article according to claim 6, wherein a space between the adjacent second positions is larger than a space between the adjacent first positions in both the longitudinal direction and the width direction so that the first region is thicker than the second region.

8. The absorbent article according to claim 5, wherein
the first concave sections are arranged in both the first and second regions of the surface member.

9. The absorbent article according to claim 5, wherein
the surface member further comprises a groove section depressed in the thickness direction and joining the absorbent member to the surface member, and
said groove section has a curve so that the absorbent article is adapted to fit along the body closely.

10. The absorbent article according to claim 9, wherein
some said first concave sections and the second concave sections are compressed together at the groove section, and
the other first concave sections and the third concave sections are compressed together at the groove section.

11. The absorbent article according to claim 5, wherein
the first region is a central region of the surface member, and the second region is a peripheral region of the surface member, the peripheral region surrounding the central region.

12. The absorbent article according to claim 3, wherein
the first concave section continuously extends in the longitudinal direction and the second concave section continuously extends in the width direction, and
the first positions where the first concave section and the second concave section intersect each other are arranged at substantially uniform density throughout an entire area of the surface member.

13. An absorbent article adapted to be worn on a wearer's body and having a longitudinal direction, a width direction, and a thickness direction, said absorbent article comprising:
an absorbent member for absorbing fluid; and
a fluid-permeable surface member covering the absorbent member, and adapted to face the body when the absorbent article is worn;
wherein
the surface member includes a surface sheet and an intermediate sheet that is disposed closer to the absorbent member than the surface sheet in the thickness direction,
the surface sheet has at least one first concave section elongated along a first direction, the first concave section being depressed toward the intermediate sheet in the thickness direction,
the intermediate sheet has at least one second concave section elongated along a second direction that intersects the first direction, the second concave section being depressed toward the surface sheet in the thickness direction, and
the surface sheet and the intermediate sheet are joined at first positions where the first concave section and the second concave section intersect each other,
said absorbent article has a front end and a rear end opposite the front end in the longitudinal direction, and
said at least one first concave section extends in the longitudinal direction all the way from the front end to the rear end.

14. The absorbent article according to claim 1, wherein the surface sheet covers the entire surface of the absorbent member.

15. An absorbent article adapted to be worn on a wearer's body and having a longitudinal direction, a width direction, and a thickness direction, said absorbent article comprising:
an absorbent member for absorbing fluid; and
a fluid-permeable surface member covering an entire surface of the absorbent member as seen in a plan view in the thickness direction, and adapted to face the body when the absorbent article is worn;
wherein
the surface member includes a surface sheet and an intermediate sheet that is disposed closer to the absorbent member than the surface sheet in the thickness direction,
the surface sheet has at least one first concave section elongated along a first direction, the first concave section being depressed toward the intermediate sheet in the thickness direction,
the intermediate sheet has at least one second concave section elongated along a second direction that intersects the first direction, the second concave section being depressed toward the surface sheet in the thickness direction,
the surface sheet and the intermediate sheet are joined at first positions where the first concave section and the second concave section intersect each other,
a plurality of the second concave sections intersect a plurality of the first concave sections to define a checker or plaid pattern as seen in the plan view,
the first direction is the longitudinal direction and the second direction is the width direction,
the surface member has a first region and a second region outside the first region;
the first and second concave sections are formed in the second region;
the intermediate sheet in the first region comprises at least one third concave section that is different from the second concave section and is spaced from the second concave section in the longitudinal direction,
the surface sheet and the intermediate sheet are joined at second positions where the first concave sections and the third concave sections intersect each other, and
in the first region, the third concave sections intersect every other first concave section.

16. An absorbent article adapted to be worn on a wearer's body and having a longitudinal direction, a width direction, and a thickness direction, said absorbent article comprising:
an absorbent member for absorbing fluid; and
a fluid-permeable surface member covering the absorbent member, and adapted to face the body when the absorbent article is worn;
wherein
the surface member includes a surface sheet and an intermediate sheet disposed closer to the absorbent member than the surface sheet in the thickness direction, the surface sheet has at least one first concave section elongated along a first direction, the first concave section being depressed toward the intermediate sheet in the thickness direction, the intermediate sheet has at least one second concave section elongated along a second direction that intersects the first direction, the second concave section being depressed toward the surface sheet in the thickness direction, the surface sheet and the intermediate sheet are joined at first positions where the first concave section and the second concave section intersect each other, a plurality of the second concave sections intersect a plurality of the first concave sections to define a checker or plaid pattern as seen in a plan view, the first direction is the longitudinal direction and the second direction is the width direction, the surface member has a first region and a second region outside the first region;

the first and second concave sections are formed in the second region;

the intermediate sheet in the first region comprises at least one third concave section that is different from the second concave section and is spaced from the second concave section in the longitudinal direction, the surface sheet and the intermediate sheet are joined at second positions where the first concave sections and the third concave sections intersect each other, and in the first region, the third concave sections intersect every other first concave section.

* * * * *